United States Patent [19]

Weinberg

[11] Patent Number: 5,324,578

[45] Date of Patent: Jun. 28, 1994

[54] PROTECTIVE ARTICLES FOR USE IN LASER SURGERY

[75] Inventor: Steven L. Weinberg, League City, Tex.

[73] Assignee: Kevtek Medical Products, Inc., League City, Tex.

[21] Appl. No.: 635,393

[22] Filed: Jan. 2, 1991

Related U.S. Application Data

[63] Continuation of Ser. No. 405,519, Sep. 11, 1989, abandoned.

[51] Int. Cl.⁵ .............................................. B32B 7/00
[52] U.S. Cl. ............................... 428/246; 428/252; 428/253; 428/254; 428/284; 428/287; 428/902
[58] Field of Search ............... 428/343, 355, 252, 289, 428/290, 253, 254, 284, 287, 902, 246

[56] References Cited

U.S. PATENT DOCUMENTS 4,601,286  7/1986  Kaufman ..................... 128/132 D
4,706,680  11/1987  Keusch et al. ................ 128/640

Primary Examiner—James J. Bell
Attorney, Agent, or Firm—Vaden, Eickenroht, Thompson, Boulware & Feather

[57] ABSTRACT

A composite of an insulative layer and a fire retardant fabric which is used to make protective articles for laser surgery and which possesses favorable burning, flashing, and resistance to burn through properties. The insulative layer is preferably a hydrogel or other hydrophilic material such as a polyurethane, collagen, polyacrylonitrile, polyvinyl alcohol, or polyvinyl acetal. The fire retardant fabric is preferably a fabric woven or knitted from polyamide or polyimide fibers having a thickness sufficient to provide the desired degree of protection.

19 Claims, No Drawings

PROTECTIVE ARTICLES FOR USE IN LASER SURGERY

This application is a continuation of co-pending application Ser. No. 07/405,519, filed on Sep. 11, 1989 is now abandoned.

BACKGROUND OF THE INVENTION

The present invention relates to articles for protection of the patient as well as surgical personnel during laser surgery. In more detail, the present invention relates to a composite for use in making articles such as gloves, surgical drapes, aprons and other items of apparel for use in protecting both patient and surgical personnel from damaged tissue resulting from direct incidence of a laser on that tissue during surgery or from fire resulting from incidence of a laser on flammable materials.

Although most damage to the skin or other tissue from a laser is repairable, the extent of the damage varies depending upon the degree of absorption of the laser wavelength and the duration of exposure such that there is potential for serious damage. Adding to that potential is the fact that reflection of the laser beam is potentially as damaging as direct contact with the beam. Various safety measures are employed depending upon the surgical procedure to protect against such damage. For instance, a back drop is used behind the tissue being lased, when possible, and in the abdominal cavity, a wet wooden tongue blade, titanium rod or wet laparotomy sponge can be used to protect underlying tissue. Abdominal and cranial cavities are filled with sterile saline to absorb the energy of the beam. Non-involved, exposed tissue is covered with wet laparotomy sponges, four by fours, or cottonoids. Patients are restrained from movement, and beaded or other non-reflective instruments are used.

Fires can occur by ignition of a drape, endotracheal tube, or article of clothing, plastic, or rubber in the treatment area. On information and belief, none of the standard surgical drapes will resist impact from a laser beam, Precautions against fire include, for instance, the covering of surgical drapes with wet towels and/or laparotomy sponges, the wetting of all the drapes, sponges and gauzes used in the area of laser application, and the precautions listed above for protecting against laser burns.

The protection provided by even the most careful application of all of these precautions simply is not sufficient. Depending upon the wavelength, time of exposure, type of laser and several other factors, the laser is capable of vaporizing these "protective" articles in exactly the same manner as the tissue on which the laser is intended to be used. There is, therefore, a need for effective protective articles for use in the treatment area.

At least one attempt has been made to provide such an article. U.S. Pat. No. 4,601,286 is directed to an "Article for the Protection of Living Tissues", said to protect ". . . living tissue from damage due to exposure to lasers . . . ". That patent describes the use of a hydrogel in the form of a drape or dressing having an opening through which the laser light can pass to impinge on the portion of the tissue to be lased, the opening having a size and shape approximating that of the tissue site to be lased (col. 5, lines 13–20, 56–60). In practice, however, such an article does not protect against laser burns; at best, such articles may provide some protection against ignition because of the high water content of the hydrogel. Experimentation has shown that penetration of a twenty-five watt or greater laser through such articles is instantaneous; further, the hydrogels are clear, making them of limited use for argon lasers which "seek" color. Penetration of the laser through the hydrogel does not appear to depend on the thickness of the hydrogel—instead, the laser penetrates instantaneously no matter what the thickness. There is, therefore, still a need for a material from which effective protective articles can be made for use in laser surgery.

SUMMARY OF THE INVENTION

The present invention satisfies that need by providing a composite for use in making protective articles for laser surgery comprising an insulative layer, which may also be adhesive in character, laminated to a layer comprised of a heat resistant, flame resistant, fire retardant fabric or fabrics. The adhesive may be any material which is more cohesive than adhesive to the surface to be protected and which is mechanically connected more firmly to the fire retardant fabric than affixed to the skin or tissue surface to be protected. The insulative layer is preferably water insoluble or hydrophilic. The fire retardant fabric is a fabric comprised of woven, knitted, braided, non-woven, or a random dispersion of polyamide, polyimide, carbon, quartz, silica, ceramic, or other fibers which is able to withstand exposure to heat and/or flame as well as those fabrics which have been treated by application of a finish that cuts off the oxygen supply around a flame. Such a composite is made into, for instance, a surgical drape, surgical gown, glove, apron, sleeve or glove protector, internal organ or eye protector, or other article for use in protecting either the patient or surgical personnel during laser surgery.

Detailed Description of the Preferred Embodiments

As used herein, the phrase "adhesive layer" refers to any material which is more cohesive than adhesive to the surface to be protected from laser damage and/or burn and which is mechanically connected more firmly to the fire retardant fabric than affixed to the surface to be protected. In a particularly preferred embodiment, the adhesive layer is a hydrogel, because such materials also provide insulation from the heat of an incident laser beam as described below. The hydrogels may be specifically a polyurethane; polyacrylonitrile; polymer of acrylic acid, methacrylic acid, ethacrylic acid, alpha-chloracrylic acid, alpha-cyanoacrylic acid, beta-methylacrylic acid (crotonic acid), alpha-phenyl acrylic acid, beta-acryloxypropionic acid, sorbic acid, angelic acid, cinnamic acid, iraconic acid, maleic acid, fumaric acid, tricarboxyethylene, maleic anhydride, vinylsulfonic acid, allyl sulfonic acid, acrylic and methacrylic sulfonic acid, sulfoethyl acrylate, and methacrylate; block polymers of poly(ethylene oxide); acrylonitrile-acrylamide copolymers; polyhydroxyalkylmethacrylares; polyacrylamide; polymethylamide; poly(N-vinyl-2-pyrrolidone); polyvinyl alcohol; hydroxylated polyvinyl alcohol; polyvinyl acetates; polyvinyl acetals; collagen; and co-polymers of styrene, ethylene, propylene, butylene, or isobutylene with maleic or fumaric anhydride. Those hydrogels available under the trademarks BIOPOL (W. R. Grace & Co.) and VIGILON (Nepara Chemical Co., Harrison, N.Y.) are particularly preferred as the adhesive layer of the present invention.

The references herein to an insulative layer are references to any material which is flexible enough to be formed into a protective article and which insulates from heat; various hydrophilic polymers, plastics and plastic films, and the hydrogels listed above, may all be used to advantage as an insulative layer in connection with the composite of the present invention as long as they are not themselves flammable or do not give off toxic fumes upon exposure to heat or flame. Particularly preferred materials for use as an insulative layer are the same hydrogels and hydrophilic polymers listed above and which also serve as the adhesive layer, specifically, polyvinyl acetals, polyvinyl alcohols, polyacrylonitrile, cellulose, and polyurethanes.

As used herein, the phrase "fire retardant fabric" refers to any high temperature resistant or fire retardant woven, knitted, braided, non-woven, or random dispersion of fibers which can be laminated to the adhesive layer to form the composite of the present invention and which, upon exposure to heat or flame, does not give off toxic fumes or by-products. Suitable fibers are nylon, polyamide (especially aramid), polyimide, carbon, quartz, fused or leached silica, ceramic, and polybenzimidazole (PBI) fibers such as are sold in fabric form under the trademarks NOMEX (E.I. dupont de Nemours & Co.), KEVLAR (E.I. dupont de Nemours & Co.), NEXTEL (3-M Company, St. Paul, Minn.) and UPJOHN 20-80. Suitable fire retardant fabrics also include those fabrics to which a fire retardant treatment has been applied such as treatment with an inorganic salt of ammonium sulfamate, zinc borate, or antimony oxychloride, chlorinated organic compounds such as chlorendic anhydride, alumina trihydrate, and certain organic phosphates and phosphonates, as well as those fabrics made from polymers to which a flame retardant chemical is chemically linked. An example of the latter is the polyester fiber sold under the trademark TREVIRA (Hoechst Fibers Industries) which, on information and belief, is a polymer of polyethylene terephthlate. The fabrics made from aramid fibers such as those sold under the trademarks NOMEX and KEVLAR are particularly preferred fire retardant fabrics for use in the composite of the present invention.

By the use of the term "laminated" herein, it is intended to refer to the joining of the insulative layer and the fire retardant fabric in such a manner as to insure the adherence of the insulative layer to the fire retardant fabric (and adhesive layer, if present) when the composite of the present invention is removed from the surface which is intended to be protected. In a presently preferred embodiment, this lamination is accomplished by embedding a layer of fire retardant fabric in a layer of a suitable hydrogel as described above. Embedding the fire retardant fabric in the hydrogel is accomplished as follows. Most hydrogels, because of their capacity for adherence, are supplied packaged between sheets of, for instance, polyethylene film. Such a three-layer package (polyethylene/hydrogel/polyethylene) is preferably laid on a flat surface and the top layer of film is pulled off of the hydrogel. The fire retardant fabric (or fabrics) is then laid on a portion of the hydrogel and the remainder of the hydrogel folded over the fabric. The hydrogel sticks to itself even better than to the fabric (hence the definition of adhesive layer set out above) such that the fabric is effectively embedded in the hydrogel with the original, remaining sheet of polyethylene film enclosing a composite constructed in accordance with the present invention. The same result is also accomplished by embedding the fire retardant fabric into the hydrogel prior to cross-linking, thus creating an integral structure after cross-linking.

Other embodiments include the use of a hydrogel having a higher adhesiveness to the fire retardant fabric than to the surface to be protected which is applied to one side of the fire retardant fabric and the use of a hydrophilic polymer and "releasable" adhesive layers comprised of adhesives such as those available from 3M Company (St. Paul, Minn.) on one side of the fire retardant fabric. Both embodiments exhibit the capability of an adhesive layer which is mechanically connected, e.g., laminated, more firmly to the fire retardant fabric than to the skin or other tissue to which it is applied. The opposite side of the fabric may also have a layer of a hydrogel laminated thereto as the insulative layer.

As a general rule, it is preferred to use fire retardant fabrics which are relatively thick. As demonstrated by the data set out below, the resistance of the composite of the present invention to burn through by a laser is directly related to increasing thickness for a particular weave and type of fabric. Particular success has also been achieved by doubling and tripling the fire retardant fabric in the fabric layer and by the use of more than one type of fabric, thereby achieving the protective thickness desired without the need for using more expensive fire retardant fabrics woven in a thick weave, for instance a pile weave. However, if desired, such thicknesses can be obtained by using single and double velour, terry, or cut weaves, or by a weft or warp knit fabric.

Other preferred composites constructed in accordance with the present invention include, for instance, those having structures such as the following:

(1) insulative layer/fire retardant fabric/insulative layer,
(2) adhesive layer/fire retardant fabric/insulative layer,
(3) insulative layer/fire retardant fabric A/fire retardant fabric B/insulative layer,
(4) insulative layer/fire retardant fabric A/adhesive or insulative layer/fire retardant fabric B/insulative layer, or
(5) insulative layer/fire retardant fabric/adhesive layer.

In this listing (1)-(5), the references to "fire retardant fabric A [and] B" are references to composites constructed in accordance with the teachings of the present invention which include two different types of fire retardant fabrics as described above.

Resistance to burn through is also improved by what might be termed "the density" of the fire retardant fabric, although changes in thickness demonstrated a greater effect on resistance than changes in density. By density, it is intended to refer to the use of coarser yarns, higher yarn counts, or tighter weaves e.g., increases in the weight of the fabric (as may be measured in, for instance, ounces per yard of fabric); in the case of non-woven and/or random dispersion fire retardant fabrics, use of the term density refers to fabrics having a higher ratio of fibers to binder.

The composite comprised of an insulative layer and a fire retardant fabric can be cut and fashioned into various protective articles such as a surgical drape, protective sleeve, apron, surgical gown, vest or jacket, back drop and/or glove. The joining of the composite is accomplished by stitching or heat bonding the fire retardant fabric. Alternatively, and particularly useful for the fashioning of such protective articles as gloves and sleeve protectors, the article is cut from fire retardant fabric and stitched or bonded together and the insulative layer is then applied to all or a portion of the fire retardant fabric of the article, e.g., in the case of a glove, to the portion of the glove which covers the back of the hand, leaving the palm and fingertips unobstructed. A three layer structure is also useful for constructing a glove in which an inner layer is comprised of the highly elastic, latex or synthetic surgical glove to which the fire retardant fabric is bonded by heating, for instance, the natural rubber or with a separate adhesive, with the insulative hydrogel being laminated to the fire retardant fabric on the outside e.g., opposite the surgical glove. Any such protective article fashioned from the composite of the present invention can then be sterilized by heat, ethylene oxide or irradiation as commonly practiced.

The following experiments conducted with the presently preferred composites are illustrative of the protection which can be achieved in accordance with the teachings of the present invention. Several composites were constructed by embedding different fire retardant fabrics in a hydrogel as described above and tested for resistance to burn through by lasers at different angles of incidence and powers. In each case, the hydrogel utilized was a 23 cm by 26 cm "custom laser drape" sold under the trademark NEURODRAPE AF (Neuromedics, Inc., Sugarland, Texas), which is packaged sterile and provided with a polyethylene liner on both sides thereof. When tested for burn through resistance with a twenty-five watt C02 laser with the laser positioned at 0.2 mm, and using a 1 cm beam width, the laser penetrated this hydrogel in less than 0.2 seconds. When power was increased to fifty watts, all other parameters remaining the same, burn through was instantaneous. The Table 1 summarizes the results obtained with the composite of the present invention, all experiments having been conducted with that same $CO_2$ laser (time to penetration given in seconds; angle of incidence approximately 90°):

TABLE 1

| COMPOSITE NO. | 1 | 2 | 3 | 4 | 5 | 6 |
|---|---|---|---|---|---|---|
| Fabric type | NOMEX | NOMEX | NOMEX | Carbon | Quartz | NOMEX |
| Thickness (inches) | 0.008 | 0.0125 | 0.016 | 0.0125 | 0.003 | 0.032* |
| Density (oz./yd.) | 2.32 | 6.5 | 6.5 | 6.5 | 300 | 13* |
| Warp × Fill | 44 × 42 | 64 × 48 | 63 × 48 | 64 × 48 | 20 × 20 | 63 × 48 |
| Weave type | plain | plain | mock | plain leno | plain | mock leno |
| Distance to composite (power) | | | | | | |
| 10 cm (50 watts) | 5 | 5 | 7 | 5 | + | |
| 1 cm (50 watts) | + | 0.2 | 0.2 | + | + | 0.6 |
| 1 cm (25 watts) | 0.2 | 0.4 | 0.4 | 0.4 | 0.2 | |

+ = instantaneous penetration
*NOMEX of same weave, density and thickness as composite number 3, doubled in thickness In a second set of experiments, a three-layer composite having the fire retardant fabric embedded within the insulative layer (e.g., insulative layer/fire retardant fabric/insulative layer), the insulative layer being a hydrogel, was tested. Again, the particular hydrogel utilized was the hydrogel sold as a laser surgery drape under the mark NEURODRAPE described above. The results are set out in Table 2, all data being the result of the use of a 30 watt $CO_2$ laser with the composite positioned five (5) cm from the laser source, and reported as seconds to burn through.

TABLE 2

| Fabric Type | Fabric Structure | Beam Orientation* 90°/45° |
|---|---|---|
| NOMEX 201 | woven | 3.1/3.7 |
| NOMEX 065 | knit (0.030") | 3.4/5.6 |
| NOMEX 078 | knit (0.021") | 3.7/5.2 |
| KEVLAR 062 | 1/16" felt | 2.8/3.7 |
| KEVLAR 678 | 1/8" felt | 5.2/4.3 |
| KEVLAR 461 | knit | 3.5/4.5 |
| KEVLAR 440 | woven | 5.8/5.8 |
| NEXTEL 508 | woven 440 | 3.9/4.0 |
| NEXTEL 671 | woven 440 | 3.1/4.7 |
| NEXTEL 805 | woven 440 | 3.0/3.6 |
| NEXTEL 507 | woven 440 | 4.8/4.5 |
| NEXTEL 3M-BF18 | woven 440 (0.017") | 3.3/ |
| control (hydrogel only)+ | | <0.2/<0.2 |

*angle of incidence of laser beam
+ = hydrogel of same thickness as hydrogel used for other composites but without fire retardant fabric embedded therein In a third set of experiments, four and five layer composites constructed in accordance with the present invention were tested in the same manner as described above in the second set of experiments. The four layer composites were of two types, type A including a layer of NOMEX type 065 fire retardant fabric and a layer of KEVLAR type 440 fire retardant fabric embedded in the same NEURODRAPE hydrogel (e.g., hydrogel/NOMEX type 065/KELVAR type 440/hydrogel). The type B four layer composite substituted a second layer of KEVLAR for the layer of NOMEX in type A (e.g., hydrogel/KEVLAR type 440/KEVLAR type 440/hydrogel). The five layer composite included hydrogel/NOMEX type 065/hydrogel/KEVLAR type 440/hydrogel, each hydrogel again being the hydrogel included in the NEURODRAPE laser surgery drape described above. All three composites were tested with a 30 watt $CO_2$ laser and were positioned five (5) cm from the laser source. The results, reported in seconds to burn through, are set out in Table 3.

TABLE 3

| | 45°* | 90°* |
|---|---|---|
| Four layer composite A | 6.5 | 6.9 |
| Four layer composite B | 7.2 | 6.8 |
| Five layer composite | 9.4 | 7.0 |

*angle of incidence of laser beam (in degrees)

Having described these presently preferred embodiments as being exemplary of the present invention as required by §112 of the Patent Statute, it is not intended that the scope of the present invention be so limited. Those skilled in the art who have the benefit of this disclosure will recognize, for instance, that there are fire retardant fabrics other than those listed above which may be used to advantage in the composite of the present invention. Likewise, adhesives other than the hydrogels described herein may be suitable for use as the adhesive or insulative layers of the composite of the present invention. All such changes and/or variations are intended to fall within the scope of the following claims.

What is claimed is:

1. A composite for use in making a protective article for laser surgery comprising an insulative layer laminated to a layer of fire retardant fabric, said layer of fire retardant fabric being comprised of two different fire retardant fabrics.

2. The composite of claim 1 additionally comprising an adhesive layer laminated to said fire retardant fabric on the side thereof opposite said insulative layer.

3. The composite of claim 2 wherein both said insulative layer and said adhesive layer are comprised of a hydrogel.

4. A protective article for use in laser surgery which is resistant to laser penetration and which is resistant to combustion and heat transfer from an incident laser beam comprising:

an insulative layer;
a layer of high temperature resistant fabric laminated to said insulative layer, said layer of high temperature resistant fabric having one or more of the characteristics of thickness,
fiber type,
density, including fiber to binder ratio, yarn coarseness, yarn count, or tightness of weave,
chemical treatment, and
weave type for conferring thereon the properties of resistance to burn through, resistance to heat transfer, and lack of production of toxic fumes when a composite comprised of said high temperature resistant fabric is struck by an incident laser beam; and
an adhesive layer laminated to the side of said layer of high temperature resistant fabric opposite said insulative layer.

5. The composite of claim 4 wherein said insulative layer is comprised of a hydrogel.

6. The composite of claim 4 wherein both said insulative layer and said adhesive layer are comprised of a hydrogel.

7. The composite of claim 6 wherein said layer of high temperature resistant fabric is embedded into the hydrogel prior to cross-linking of the hydrogel.

8. The composite of claim 4 wherein the desired thickness of said high temperature resistant fabric is obtained by using a fire retardant fabric having a pile, single or double velour, terry, or cut weave, or by using a weft or warp knit, or by using multiple layers of fabric to comprise said layer of high temperature resistant fabric.

9. The composite of claim 4 wherein said layer of high temperature resistant fabric is comprised of two layers of fire retardant fabric.

10. The composite of claim 4 wherein the density of said layer of high temperature resistant fabric ranges from 2.32 to 300 oz/yd.

11. A protective layer for use in laser surgery which resists combustion, heat transfer, and penetration by an incident laser beam comprising an insulative layer having a layer of high temperature resistant fabric laminated thereto, said layer of high temperature resistant fabric being of sufficient thickness, sufficient density, or a combination of sufficient thickness and sufficient density, to provide sufficient resistance to penetration by an incident laser beam so as to protect a person from a burn resulting therefrom.

12. The composite of claim 11 additionally comprising an adhesive layer.

13. The composite of claim 12 wherein both said insulative and said adhesive layer are comprised of a hydrogel.

14. The composite of claim 13 wherein said layer of high temperature resistant fabric is embedded into the hydrogel prior to cross-linking the hydrogel.

15. The composite of claim 13 additionally comprising a sheet of polyethylene enclosing said composite.

16. The composite of claim 11 wherein sufficient density of said layer of high temperature resistant fabric is achieved by using a fire retardant fabric having a coarse yarn, high yarn count, tight weave, or high ratio of fiber to binder as said layer of high temperature resistant fabric.

17. The composite of claim 11 wherein sufficient thickness of said layer of high temperature resistant fabric is achieved by using a fire retardant fabric having a pile, single or double velour, terry, or cut weave, or by using a fire retardant fabric having a weft or warp knit, or by using multiple layers of fire retardant fabric to comprise said layer of heat resistant fabric.

18. The composite of claim 11 wherein the density of said layer of high temperature resistant fabric is between 2.32 and 300 oz/yd.

19. The composite of claim 11 wherein the thickness of said layer of high temperature resistant fabric ranges from 0.003 to 0.125 inches.

* * * * *